United States Patent [19]

Zanger

[11] Patent Number: 5,324,180
[45] Date of Patent: Jun. 28, 1994

[54] SURGICAL INSTRUMENT WITH DRAWER LOADING CASSETTE SYSTEM

[75] Inventor: Frank Zanger, Hayward, Calif.

[73] Assignee: Allergan, Inc., Irvine, Calif.

[21] Appl. No.: 105,461

[22] Filed: Jun. 7, 1993

Related U.S. Application Data

[63] Continuation of Ser. No. 940,659, Sep. 4, 1992, abandoned.

[51] Int. Cl.5 ............................................. F04B 43/12
[52] U.S. Cl. .................................. 417/475; 417/477 R
[58] Field of Search ............... 417/474, 475, 476, 477, 417/478, 479; 604/151, 152, 153; 128/DIG. 12

[56] References Cited

U.S. PATENT DOCUMENTS

| | | | |
|---|---|---|---|
| 4,187,057 | 2/1980 | Xanthopoulos | 417/477 |
| 4,537,561 | 8/1985 | Xanthopoulos | 417/477 |
| 4,548,553 | 12/1985 | Ferster | 417/477 |
| 4,673,334 | 6/1987 | Allington et al. | 417/477 |
| 4,713,051 | 12/1987 | Steppe et al. | 604/30 |
| 4,735,558 | 4/1988 | Kienholz et al. | 417/477 |
| 4,798,580 | 1/1989 | DeMeo et al. | 417/476 |
| 4,886,431 | 12/1989 | Soderquist | 417/477 |

FOREIGN PATENT DOCUMENTS

| | | |
|---|---|---|
| 0362822 | 11/1990 | European Pat. Off. . |
| 91/06325 | 5/1991 | PCT Int'l Appl. . |
| 2076476 | 12/1981 | United Kingdom ............... 417/477 |

*Primary Examiner*—Richard A. Bertsch
*Assistant Examiner*—Roland G. McAndrews, Jr.
*Attorney, Agent, or Firm*—Walter A. Hackler

[57] ABSTRACT

A drawer loading cassette system for a surgical instrument includes a control cabinet and an assembly head disposed therein which includes a plurality of rollers mounted in circular pattern with each roller having a rotation axis generally parallel to an assembly heads central axis. The assembly head is mounted in the cabinet for rotation about the assembly head central axis and a drawer, configured for engagement with a tubing management cassette, is movably attached to the cabinet in order to provide an open position for loading the the cassette and a closed position for engaging a section of tubing supported by the cassette with the rollers.

12 Claims, 5 Drawing Sheets

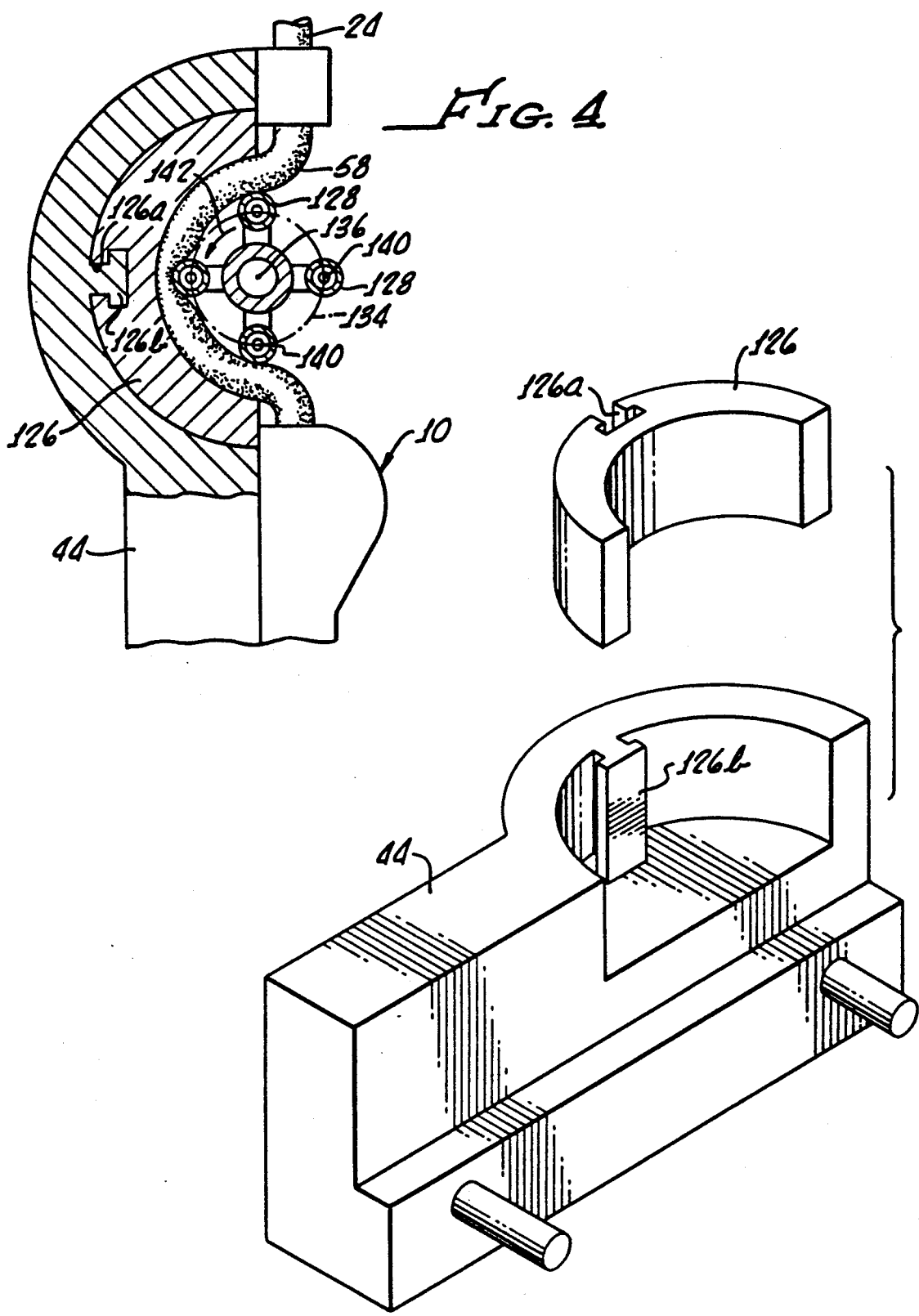

SURGICAL INSTRUMENT WITH DRAWER LOADING CASSETTE SYSTEM

This is a continuation of copending application Ser. No. 07/940,659 filed on Sep. 4, 1992, now abandoned.

The present invention generally relates to irrigation-/aspiration apparatus for surgical procedures and more particularly relates to a drawer loaded cassette system for use with a surgical instrument for endophthalmic surgery, enabling in-field modification to provide a custom support system for such surgical instrument.

The removal of cataracts, for example, involves surgery on a normally pressurized eye in which instruments are passed through a small incision at the edge of the cornea in order to access and remove opaque cataract material.

The cataracts may be fragmentized by cutting apparatus, vibratory apparatus, or the like, and the fragments are aspirated from the eye.

In order to maintain normal pressure within the eye, a balanced salt solution is supplied from an elevated chamber, the chamber being elevated to a position to provide proper head, or pressure.

The irrigation and aspiration of fluid through the eye must be carefully monitored in order to maintain normal pressure within the eye during surgical procedures. An under-pressure may cause distortion of the eye which often may interfere with surgical procedures. Over pressure may cause damage to the eye and in extreme cases, rupture thereof.

As it has been hereinabove noted, pressure in the eye may be controlled by the physical elevation of the chamber of balanced salt solution, which is connected to the surgical instrument. Aspiration fluid, on the other hand, is controlled in the eye with a peristaltic pump.

Typical apparatus includes instrument console for controlling the flow of fluids. Various devices have been developed for the coordinated flow of fluids and some include a phacocassette, tubing and management system, which may be disposable or autoclavable, for interconnecting from the various tubes and lines for proper irrigation and aspiration.

A general discussion of the advantages of this type of cassette is set forth in U.S. Pat. No. 4,713,051.

Cassettes, such as those described in U.S. Pat. No. 4,713,051, provide means for housing a portion of each of the irrigation and aspiration tubing, together with a drain bag structured so that all fluid and connections are precisely made to the equipment by insertion of the cassette into a console. Thus, the reliability of the fluid connections is enhanced.

While the prior art devices, such as the one described in U.S. Pat. No. 4,713,051, provide a significant step forward in the art up to management, these devices do not provide full cooperation with a surgical instrument utilizing irrigation and aspiration lines. In addition, in-field modification is not provided by such prior art devices.

For example, during surgical procedures, often fragments of broken tissue can temporarily block an aspiration line. This may lead to a serious deviation in pressure which is typically accommodated by ceasing or slowing aspiration through regulation of the peristaltic pump connected to the aspiration line. In addition, fluid flow may be temporarily reversed so that the blockage may be dislodged. None of these procedures are handled by prior art tubing management systems.

However, the tubing management system, in accordance with the present invention, facilitates the reversal of fluid flow in a surgical instrument's irrigation and aspiration lines. Naturally, this facilitates operating procedures and, at the same time, provides increased reliability of high pressure during an operation. In addition, accommodation for different tubing and operating procedure may be provided by the present invention with such accommodation being possible on an "on the spot" basis by an operating attendant.

SUMMARY OF THE INVENTION

A drawer loading cassette system in accordance with the present invention for surgical instruments generally includes a control cabinet and an assembly head comprising a plurality of rollers, with each roller being rotatably mounted in a circular pattern about an assembly head control axis, and each roller having a rotation axis generally parallel to the assembly head central axis.

Alternatively, a plurality of assembly heads may be provided with each comprising a plurality of rollers with each roller being rotatably mounted in a circular pattern about the assembly head central axis. In this embodiment, each of these assembly heads may have a different number of rollers for providing in combination with arcuate surface members, hereinafter described, various flow patterns through a tube supported by a cassette, as hereinafter described.

The drawer-loading cassette system in accordance with the present invention, further includes means for mounting each of the assembly heads in the cabinet for rotation about the assembly head axis and a drawer, configured for engagement with a tubing management cassette, is provided and removably attached in the cabinet in order to provide an open position, enabling loading of the cassette thereinto, and a closed position, causing engagement of the rollers with a section of tubing supported by the cassette.

Importantly, means are disposed in the drawer for causing the rollers to successively contact, gradually compress and seal the tubing section and thereafter, gradually decompress the tubing section in order to move a fluid through the tubing section in one direction.

More particularly, the means for causing the plurality of rollers to contact the present seal tube comprises an arcuate surface member in the drawer and a position enabling the rollers to contact, compress and seal the tube when the drawer is in a closed position.

Preferably, in accordance with the present invention, this includes a plurality of arcuate surface members with a select arcuate surface member removably mounted in the drawer. This feature, in combination, with the plurality of assembly heads, hereinabove discussed, provides the advantage of modifying the system to accommodate for various types of tubing or surgical procedures. Accordingly, modification, by way of changing the arcuate surface member disposed in the drawer and the assembly head mounted in the cabinet, may be performed in the field by an attendant, as may be required, or at the discretion of the attendant and the surgeon.

BRIEF DESCRIPTION OF THE DRAWINGS

The advantages and features of the present invention will be better understood by the following description when considered in conjunction with the accompanying drawings in which:

FIG. 4 is a cross-sectional view of the assembly head and arcuate surface member, showing a plurality of rollers for compressing a resilient tube;

FIG. 5 is an exploded view of one of a plurality of arcuate surface members, as it may be removably mounted in the drawer;

DETAILED DESCRIPTION

Figure 1:
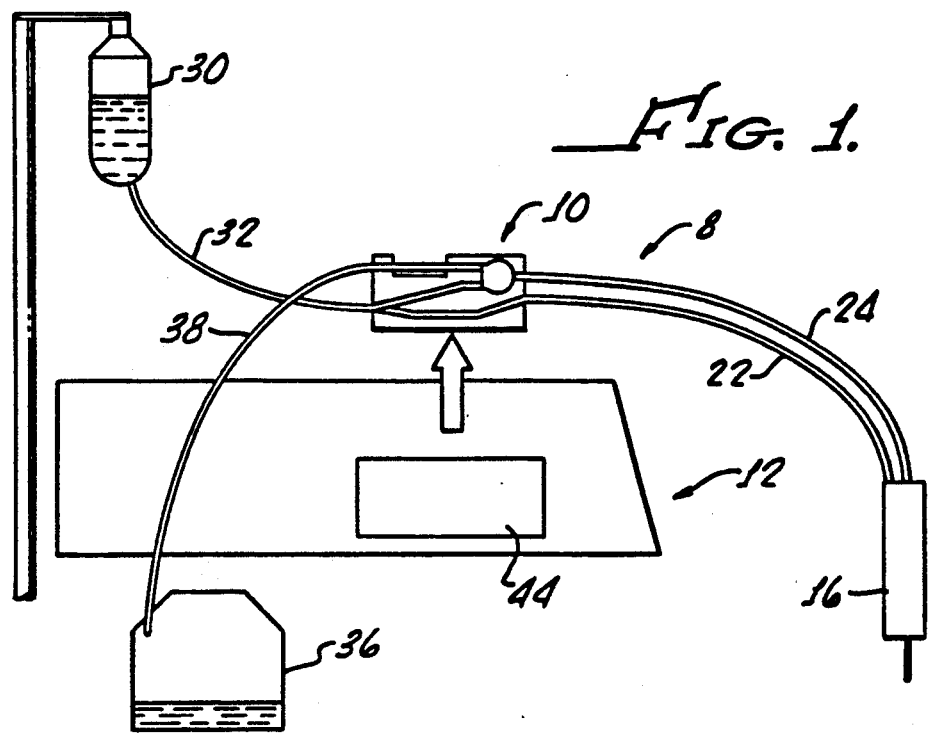
FIG. 1 is a schematic representation of the present invention showing interconnection between a surgical instrument, a saline solution supply, and a waste receptacle.

In FIG. 1, there is shown, in a conceptual format, surgical instrument system 8 with drawer loading cassette system 10, including a control cabinet 12 having an assembly head 14 (see FIG. 2), and a surgical instrument 16 (see FIG. 1).

Figure 2:
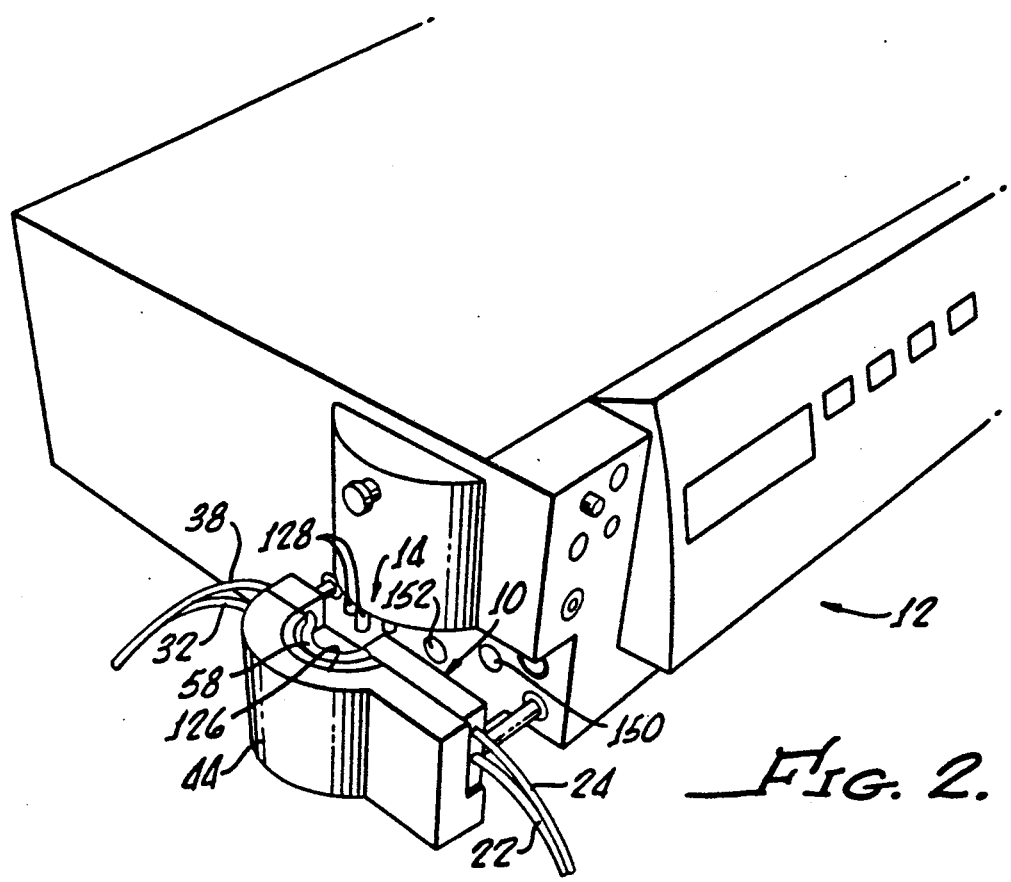
FIG. 2 is a perspective view of a tubing management cassette as it may be inserted into a drawer and control cabinet.
Figure 3:
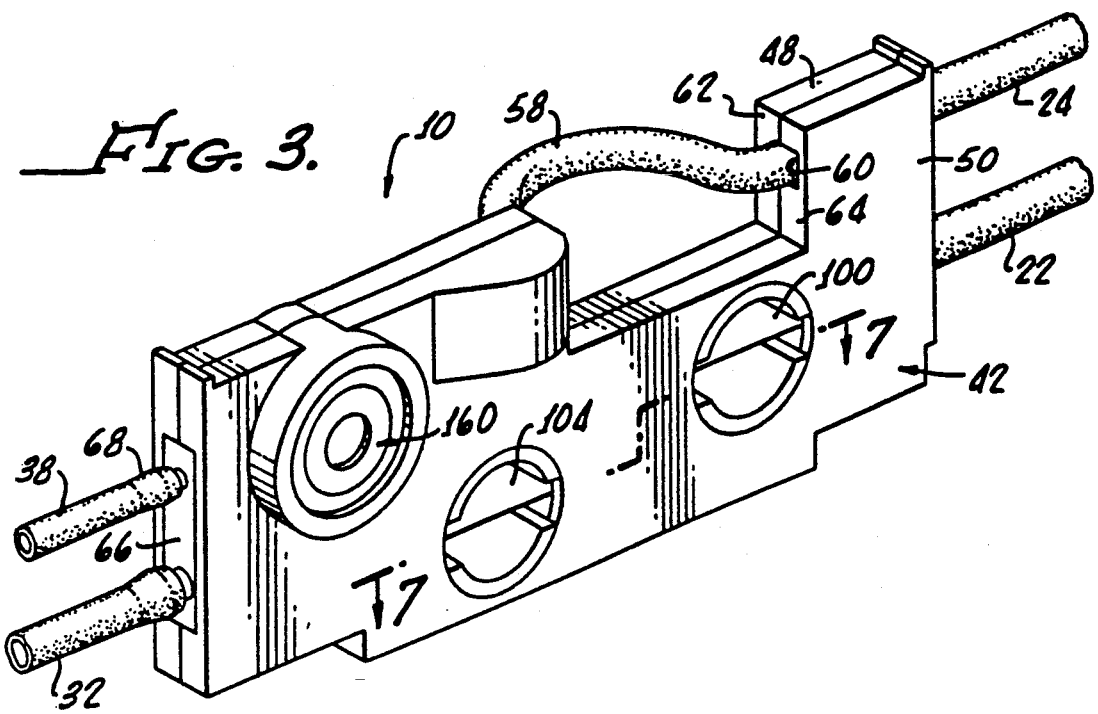
FIG. 3 is a perspective view of the tubing management cassette suitable for use with the present invention.

As hereinabove described, the present invention is used in conjunction with the surgical instrument or handpiece 16 for ophthalmic surgery, requiring irrigation and aspiration of fluids. As will be hereinafter discussed in greater detail, the cassette 10 is connected with an irrigation line 22 and an aspiration line 24 for providing fluid communication between the surgical handpiece 16 and a source 30 of balanced saline solution (BSS) through a BSS line 32 and also with a waste receptacle 36 through a waste line 38. All these are diagrammatically represented in FIG. 1. As will be described hereinafter in greater detail, the cassette 10 includes a housing 42 (FIG. 3) which is sized for insertion into a drawer 44 in the cabinet 12 (FIG. 2).

A suitable cassette for the present invention is described in U.S. patent application entitled "Tubing Management System," Ser. No. 07/893,119, filed Jun. 3, 1992. This application is herewith incorporated by reference thereto, including all drawings and specification. Briefly, the cassette 10 may include a housing 42 which may consist of the rear half 48 and a front half 50 which is formed from any suitable plastic material. If the cassette 10 is disposable, the rear and front halves 48 and 50 may be plastic welded or glued together to form the cassette 10. In this instance, a lower grade of plastic for the cassette 10 may be employed.

Alternatively, if the cassette is to be reused, the rear and front halves 48 and 50 may be snapped or screwed together in any suitable fashion in order to facilitate disassembly of the cassette 10. In this instance, the rear and front halves 48 and 50 should preferably be formed from a plastic suitable for autoclaving.

The rear half 48 includes a channel 60 in order to provide a means for supporting a tube section 58 when the rear half 48 is assembled to the front half to form the housing 42. Opening 62 in the rear half 48 and opening 64 in the front half 50 enable access to an aspiration tube section 58 for contact with the drawer 44 and an assembly head 14 (see FIG. 2) as hereinafter described. A manifold 66 includes a nipple 68 which provides means for connecting the aspiration tube section 58 with the waste line 38.

Transfer tubes 100, 104 interconnect the irrigation lines 22, 32 and aspiration line 24 of the surgical instrument 16, as described in U.S. patent application Ser. No. 07/893,119, hereinabove referenced.

The upper transfer tube 100 is centered in the opening 114 in the front half 50 and the lower transfer tube 104 is centered in opening 116 in the front half and the openings 114, 116 provide a means for enabling the regulation of irrigation fluid flow in the irrigation line 32 into both the irrigation line 22 and aspiration line 24 of the surgical instrument 16.

Figure 7:
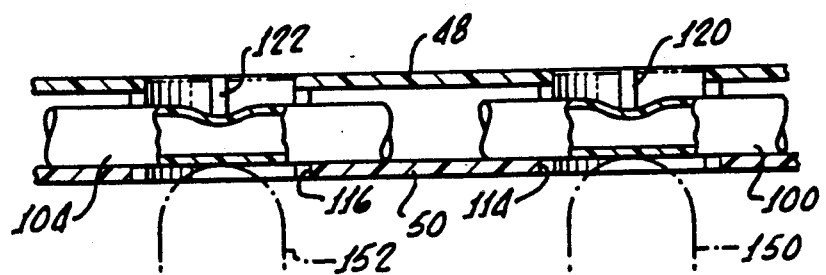
FIG. 7 is a cross-sectional view of the tubing management system taken along the line 8—8 of FIG. 3, showing compression of transfer tubes therein for controlling fluid flow by control element in the control cabinet.

Bridges 120, 122 (see FIG. 7), formed in the front half 50 and spanning the openings 114, 116 respectively, provide a means for enabling the transfer tubes 100, 104 to be compressed, as hereinafter described, in order to regulate the fluid flow in the transfer tubes 100, 104 and thereby divert irrigation fluid from the BSS line 32 into either the irrigation line 22 or aspiration line 24 of the surgical instrument 16.

Turning now to FIG. 2, the console drawer 44 is sized for accepting the cassette 10 in the manner illustrated. An arcuate surface member 126 provides means for controlling contact of the tubing section 58 with rollers 128 in order to move a fluid through the tubing. As shown in FIG. 5, the arcuate surface member 126 may be removably mounted to the drawer 44 by by a slot 126A and guide 126B in order to prevent relative movement between the member 126 and the drawer 44. Any other conventional means (not shown) may be employed to removeably attach the member 126 to the drawer 44. A plurality of arcuate surface members 126, each having different curvature and size, may be provided in order to provide selected pumping characteristics or accommodate different tubing with various diameters and wall thicknesses.

A teaching of the type of arcuate surface suitable for use with the present invention may be found in U.S. patent application entitled "Reduced Pulsation Tapered Ramp Pump Head," Ser. No. 07/892,788, filed Jun. 3, 1992. This reference including all drawings and specification is to be incorporated into the present application by this specific reference thereto.

In brief review of the disclosure set forth in U.S. Ser. No. 07/892,788, an assembly head 14 includes the plurality of rollers 128 with each roller 128 being rotatably mounted in a circular pattern 134 about an assembly head central axis 136, with each roller having a rotation axis 140, which is generally parallel to the assembly head.

As shown in FIG. 4, the arcuate surface member 126 is configured and positioned with respect to the assembly head 130 so that, as the assembly head 130 is rotated in the direction of arrow 14, each roller 128 successively contacts the tube section 58, gradually compressing and sealing the tube section 58 during approximately a 45° rotation of the assembly head 14.

Further configuration of the arcuate surface member 126 and position thereof with respect to the assembly head 14 enables each roller to gradually release the tube section 58 during a rotation of the assembly head 14 of about 45°. This configuration also enables each roller to remain in a sealing engagement with the tube section 58 during approximately a 90° rotation of the assembly head 14.

Figure 6:
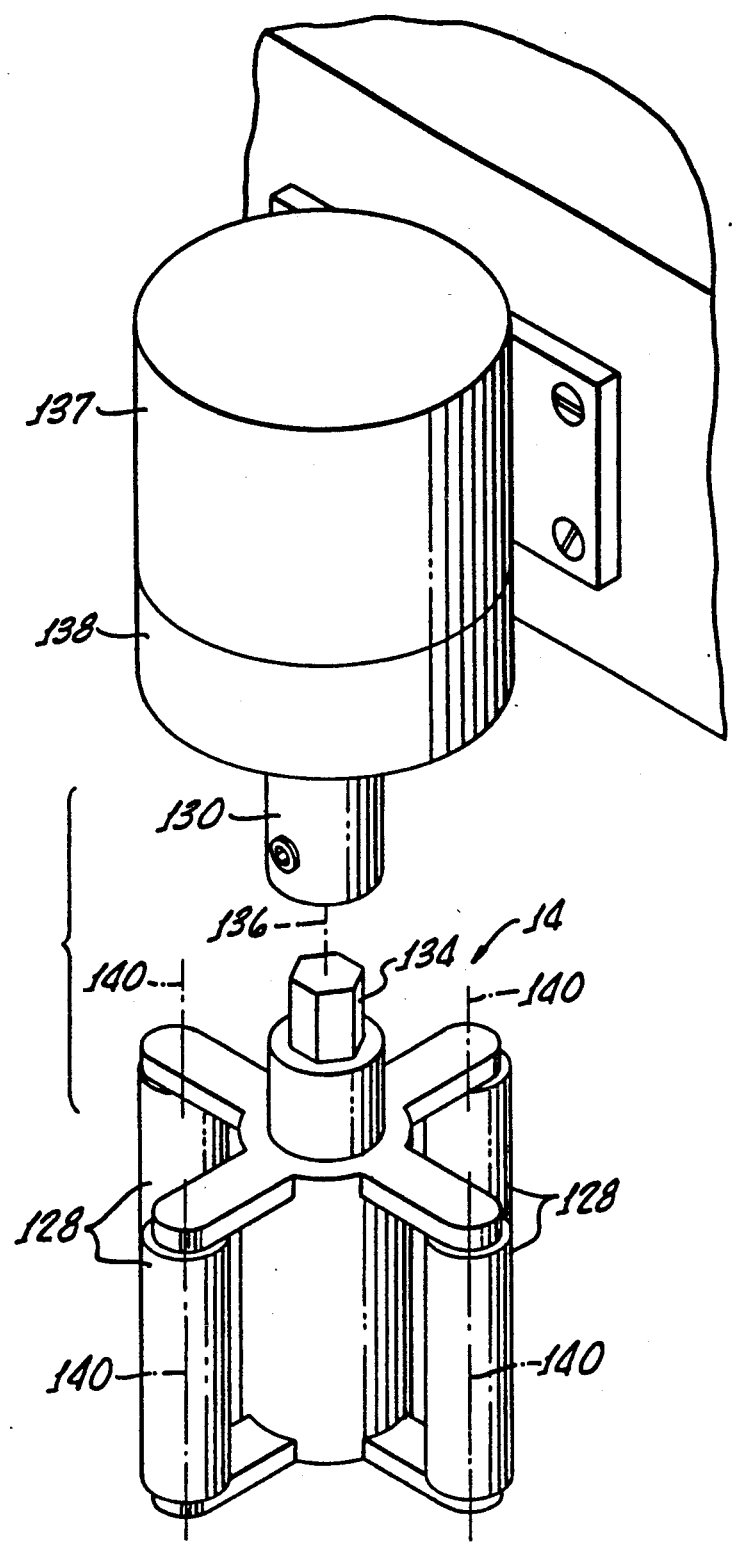
FIG. 6 is an exploded view of one of a plurality of assembly heads as it may be mounted in the control cabinet.
Figure 8:
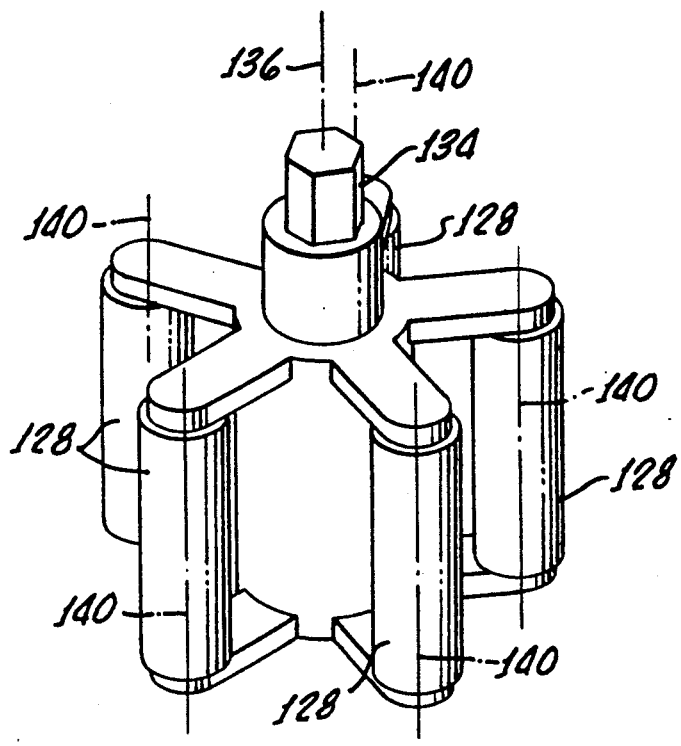
FIG. 8 is a perspective view of another of the plurality of assembly heads as may be used with the present invention.

As shown in FIG. 6, the assembly head 14 may be removably mounted in the cabinet by a collet 130 and shaft 134. The collet 130 may be driven by a motor 137 through a gear box 138. This enables easy exchange thereof for changing pumping characteristics in the tube section 58. The pumping characteristic being, of course, also dependent on the arcuate surface member 126, the details of which are set forth in U.S. patent application, Ser. No. 07/892,788.

The drawer 44 may be mounted to the cabinet in any conventional manner to enable it to be moved from an open position, enabling loading of the cassette 10 to a closed position, causing engagement of the rollers with the tube section 58.

Also included in the cabinet 12 are solenoid-activated plungers 150, 152 which, when activated, move outwardly from the console to engagement with the transfer tubes 100, 104 respectively through the holes 114, 116, in order to compress the transfer tubes 100, 104 against the bridges 120, 122, respectively, in the rear half 48, in order to control irrigation fluid flow.

The plungers 150, 152 may be activated and operated in any conventional manner through switches in the console 12 or by remote control, as may be desired.

While not part of the present invention, the cassette 10, a transducer 160, may be included which provides a means for measuring force exerted by fluid within the tubing 58. A description of this type of transducer is to be found in U.S. patent application Ser. No. 07/893,331, filed Jun. 3, 1992, entitled "Pressure Transducer Interface". This reference is incorporated into the present application by this specific reference thereto.

Although there has been hereinabove described a drawer-loading cassette system, in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. Drawer loading cassette system for a surgical instrument, said system comprising:

a control cabinet;

an assembly head disposed in the control cabinet and comprising a plurality of rollers, each roller being rotatably mounted in a circular pattern about an assembly head central axis, each roller having a rotation axis generally parallel to the assembly head central axis;

means for mounting said assembly head in said control cabinet for rotation about the assembly head central axis;

a tubing management cassette comprising means for supporting an aspiration tube section and for enabling access to the tube section for compression by said plurality of rollers and means for supporting transfer tubes and for enabling access thereto from the control cabinet;

a drawer configured for engagement with the tubing management cassette, said drawer being slidably attached to said control cabinet for translational movement in order to provide an open position enabling loading of the cassette thereinto, and a closed position causing engagement of the rollers with the aspiration tube section supported by the tubing management cassette;

means, separate from said tubing management cassette and removably disposed in said drawer, for directly contacting the aspiration tube section and for causing said rollers to successively contact, gradually compress and seal the aspiration tube section and thereafter gradually decompress the aspiration tube section in order to move a fluid through the aspiration tube section in one direction; and means, disposed in said control cabinet for engaging the transfer tubes supported by the tubing management cassette and compressing the transfer tubes in order to control irrigation fluid flow.

2. The system according to claim 1 wherein said means for causing said plurality of rollers to contact, compress and seal the tube comprises an arcuate surface member mounted in said drawer in a position enabling said rollers to contact, compress and seal the tube with the drawer in the closed position.

3. The system according to claim 1 wherein said means for causing said plurality of rollers to contact, compress and seal the tube comprises a plurality of arcuate surface members, each member adapted for being removably mounted in said drawer in a position enabling said rollers to contact, compress and seal the tube with the drawer in the closed position.

4. The system according to claim 3 further comprising means for aligning said tubing management cassette with instrument controls disposed in said control cabinet.

5. Drawer loading cassette system for a surgical instrument, said system comprising:

a control cabinet;

an assembly head disposed in the control cabinet and comprising a plurality of rollers, each roller being rotatably mounted in a circular pattern about an assembly head central axis, each roller having a rotation axis generally parallel to the assembly head central axis;

means for mounting said assembly head in said control cabinet for rotation about the assembly head central axis;

a tubing management cassette comprising means for supporting an aspiration tube section and for enabling access to the tube section for compression by said plurality of rollers and means for supporting transfer tubes and for enabling access thereto from the control cabinet;

a drawer configured for engagement with a tubing management cassette, said drawer being slidably attached to said cabinet for translational movement in order to provide an open position enabling loading of the cassette thereinto, and a closed position causing engagement of the rollers with the aspiration tube section supported by the cassette;

means separate from said tubing management cassette and removably disposed in said drawer for directly contacting said aspiration tube section and for controlling contact of the aspiration tube section with said rollers in order to move a fluid through the aspiration tube section; and means, disposed in said control cabinet for engaging the transfer tubes supported by the tubing, management cassette and compressing the transfer tubes in order to control irrigation fluid flow.

6. The system according to claim 5 wherein said means for controlling contact of the tubing section with said rollers comprises an arcuate surface member mounted in said drawer in a position enabling said rollers to contact, compress and seal the tubing section when the drawer is in the closed position.

7. The system according to claim 5 wherein said means for controlling contact of the tubing section with said rollers comprises a plurality of arcuate surface members, each member adapted for being removably mounted in said drawer in a position enabling said rollers to contact, compress and seal the tube when the drawer is in the closed position.

8. The system according to claim 7 further comprising means for aligning said tubing management cassette with instrument controls disposed in said control cabinet.

9. Drawer loading cassette system for a surgical instrument, said system comprising:

a control cabinet;

a plurality of assembly heads, each configured for individual mounting in said control cabinet, each assembly head comprising a plurality of rollers, each roller being rotatably mounted in a circular pattern about an assembly head central axis, each roller having a rotation axis generally parallel to the assembly head central axis;

means for removably mounting one of said assembly heads in said control cabinet for rotation about the assembly head central axis;

a tubing management cassette comprising means for supporting an aspiration tube section and for enabling access to the tube section for compression by said plurality of rollers and means for supporting transfer tubes and for enabling access thereto from the control cabinet;

a drawer configured for engagement with a tubing management cassette, said drawer being slidably attached to said cabinet for translational movement in order to provide an open position enabling loading of the cassette thereinto, and a closed position causing engagement of the rollers with the aspiration tube section supported by the cassette;

means, separate from said tubing management cassette and removably disposed in said drawer, for directly contacting said aspiration tube section and causing said rollers to successively contact, gradually compress and seal the aspiration tube section and thereafter gradually decompress the aspiration tube section in order to move a fluid through the aspiration tube section in one direction; and means, disposed in said control cabinet for engaging the transfer tubes supported by the tubing management cassette and compressing the transfer tubes in order to control irrigation fluid flow.

10. The system according to claim 9 wherein said means for causing said plurality of rollers to contact, compress and seal the tube comprises an arcuate surface member mounted in said drawer in a position enabling said rollers to contact, compress and seal the tube when the drawer is in the closed position.

11. The system according to claim 9 wherein said means for causing said plurality of rollers to contact, compress and seal the tube comprises a plurality of arcuate surface members, each member adapted for being removably mounted in said drawer in a position enabling said rollers to contact, compress and seal the tube when the drawer is in the closed position.

12. The system according to claim 11 further comprising means for aligning said tubing management cassette with instrument controls disposed in said control cabinet.

* * * * *